US006548285B1

(12) United States Patent
Swinkels et al.

(10) Patent No.: US 6,548,285 B1
(45) Date of Patent: Apr. 15, 2003

(54) **POLYNUCLEOTIDES ENCODING *ASPERGILLUS NIGER* AND *PENICILLIUM CHRYSOGENUM* ACETAMIDASES AND METHODS OF USE AS SELECTABLE MARKERS**

(75) Inventors: Bart W. Swinkels, Delft (NL); Gerardus C. M. Selten, Berkel En Rodenrijs (NL); Janna G. Bakhuis, Delft (NL); Roelof A. L. Bovenberg, Rotterdam (NL); Adrianus W. H. Vollebregt, Naaldwijk (NL)

(73) Assignee: DSM N.V. (NL)

( * ) Notice: Subject to any disclaimer, the term of this patent is extended or adjusted under 35 U.S.C. 154(b) by 0 days.

(21) Appl. No.: 08/809,955

(22) PCT Filed: Aug. 5, 1996

(86) PCT No.: PCT/EP96/03494

§ 371 (c)(1),
(2), (4) Date: Apr. 3, 1997

(87) PCT Pub. No.: WO97/06261

PCT Pub. Date: Feb. 20, 1997

(30) Foreign Application Priority Data

Aug. 3, 1995 (EP) .......................................... 95202129

(51) Int. Cl.[7] .......................... C12N 9/80; C12N 15/00; C12N 1/14; C07H 21/04

(52) U.S. Cl. ............... 435/228; 435/320.1; 435/254.11; 435/252.3; 435/69.1; 536/23.2

(58) Field of Search ............................. 435/228, 252.3, 435/320.1, 254.11, 254.2, 69.1; 536/23.2

(56) References Cited

FOREIGN PATENT DOCUMENTS

EP 0 635 574 A1 1/1995

OTHER PUBLICATIONS

Chang, T. et al., Nucl. Acids Res., vol. 18, No. 23, p. 7180, 1990.*

Gomi, K. et al., Gene, vol. 108, No. 1, pp. 91–98, 1990.*

Corrick, C. et al., Gene, vol. 53, pp. 63–71, Jul. 13, 1987.*

Kuwahara, M. et al., J. Ferment. Technol., vol. 59, No. 6, pp. 573–577, 1980.*

Van der Walt, J. et al., System. Appl. Microbiol., vol. 16, pp. 330–332, 1993.*

Price, V. et al., Meth. Enzymol., vol. 185, pp. 308–318, 1990.*

Lee, C.C. et al., Science, vol. 239, No. 239, pp. 1288–1291, 1988.*

Masuda, Y. et al., Curr. Gen., vol. 25, pp. 412–417, 1994.*

Hashimoto, Y. et al., Bioch. Biophys. Acta, vol. 1088, pp. 225–233, 1991.*

Beri, R.K., et al., "Transformation of *Penicillium chrysogenum* using the *Aspergillus nidulans* amdS gene as a dominant selective marker," *Curr Genet* (1987) 11:639–641.

Brammar, W.J., et al., "The nucleotide sequence of the amiE gene of *Pseudomonas aeruginosa*," *FEBS Letters* (1987) 215(2):291–294.

Christensen, T., et al., "High Level Expression of Recombinant Genes in *Aspergillus oryzae*," *Bio/Technology* (1988) 6:1419–1422.

Hynes, M.J., et al., "The Genetic Analysis of Regulation of Amidase Synthesis in *Aspergillus nidulans*," *Molec Gen Genetics* (1970) 108:107–116.

Katsuya, G., et al., "Cloning and molecular characterization of the acetamidase–encoding gene *(amdS)* from *Aspergillus oryzae*," *Gene* (1991) 108:91–98.

Kelly, J.M., et al., "Transformation of *Aspergillus niger* by the *amdS* gene of *Aspergillus nidulans*," *The EMBO Journal* (1985) 4(2):475–479.

Mahenthiralingam, E., et al., "Cloning and sequencing of the gene which encodes the highly inducible acetamidase of *Mycobacterium smegmatis*," *Journal of General Microbiology* (1993) 139:575–583.

Pe'er, S., et al., "Stability of *Trichoderma harzianum amdS* Transformants in Soil and Rhizosphere," *Soil Biol Biochem* (1991) 23(11):1043–1046.

Penttilä, M., et al., "A versatile transformation system for the cellulolytic filamentous fungus *Trichoderma reesei*," *Gene* (1987) 61:155–164.

Tilburn, J., et al., "Transformation by integration in *Aspergillus nidulans*," *Gene* (1983) 26:205–221.

Ward, M., et al., "Use of *Aspergillus* overproducing mutants, cured for integrated plasmid, to overproduce heterologous proteins," *Appl Microbiol Biotechnol* (1993) 39:738–743.

* cited by examiner

*Primary Examiner*—Rebecca E. Prouty
*Assistant Examiner*—David J Steadman
(74) *Attorney, Agent, or Firm*—Morrison & Foerster LLP

(57) ABSTRACT

The present invention discloses novel amdS genes from fungi previously not known to contain an amdS gene, such as *Aspergillus niger* and *Penicllium chrysogenum*. The novel amdS genes can be used as homologous selectable marker genes in the transformation of these fungi. Alternatively, the cloned amdS genes can be used to inactivate the endogenous copy of the gene in order to reduce the background in transformation experiments.

13 Claims, 4 Drawing Sheets

```
        125
A.nid   PISLKDQLRV   KGYETSMGYI   SWLNKYD...   ......EGDS
A.ory   PISLKDQLRV   KGTETCMAYI   SWLGKRD...   ......TSDS
S.cer   PISLKDQCNV   EGVDTSLGYL   CRTFKPKTK.   ......NEES
A.nig   PVSLKDQFHV   KGVETTMGYV   GWINTFQGKT   NDPRYLTHES
P.chr   PIWLKDQFNV   KGVDTTLGYV   GRSFAPA...   ......QEDA

        156
A.nid   VLTTMLRKAG   AVFYVKTSVP   QTLMVCETVN   NIIGRTVNPR
A.ory   ILTALLRKAG   AVFLVKTSVP   QTLMVCETVN   NIIGRTSNPR
S.cer   LIVSFLRDLG   AIIFVKTTVP   SSMMATDTQS   NTFGYTYNSI
A.nig   ELVKELRAAG   AVLYCKTSVP   MTLMSGETMN   NIITYTHNPK
P.chr   VLVQILKNMG   AIVIAKTNIP   QSIMVAETEN   PLWGLTTNPR

        196                                    226
A.nid   NKNWSCGGSS   GGEGAIVGIR   GGVIGVGTDI   G
A.ory   NLNLSCGGSS   GGEGAMIAMR   GGAIGIGTDI   G
S.cer   NLSFSSGGSS   GGEGSLIGAH   GSLLGLGTDI   G
A.nig   NRLLSSGGSS   GGEGALIALR   GSPAGFGTDI   G
P.chr   NPIFSPGGST   GGEGALLALH   GSLFGFGTDI   G
```

Figure 1A

| Amino acid positional identity of *amd*S internal consensus fragments | | | | | |
|---|---|---|---|---|---|
| *A.nid* | -- | | | | |
| *A.ory* | 80 | -- | | | |
| *S.cer* | 47 | 46 | -- | | |
| *A.nig* | 60 | 60 | 47 | -- | |
| *P.chr* | 48 | 47 | 53 | 53 | -- |
| | *A.nid* | *A.ory* | *S.cer* | *A.nig* | *P.chr* |

Figure 1B

POLYNUCLEOTIDES ENCODING *ASPERGILLUS NIGER* AND *PENICILLIUM CHRYSOGENUM* ACETAMIDASES AND METHODS OF USE AS SELECTABLE MARKERS

FIELD OF THE INVENTION

The present invention relates to the field of molecular biology, in particular the invention is concerned with selectable marker genes to be used in transformation of organisms.

BACKGROUND OF THE INVENTION

The *Aspergillus nidulans* amdS gene is probably the most frequently used selectable marker for the transformation of filamentous fungi and has been applied in most of the industrially important filamentous fungi such as e.g. *Aspergillus niger* (Kelly and Hynes 1985, EMBO J. 4: 475–479), *Penicillium chrysogenum* (Beri and Turner 1987, Curr. Genet. 11: 639–641), *Trichoderma reesei* (Pentillä et al. 1987, Gene 61: 155–164), *Aspergillus oryzae* (Christensen et al. 1988, Bio/technology 6: 1419–1422) and *Trichoderma harzianum* (Pe'er et al. 1991, Soil Biol. Biochem. 23: 1043–1046).

The popularity of the amdS gene as a selectable marker is most likely a result of the fact that it is the only available non-antibiotic marker gene which can be used as a dominant selectable marker in the transformation of fungi. Dominant selectable markers provide the advantage that they can be used directly in any strain without the requirement for mutant recipient strains. The antibiotic-resistance genes are, however, not preferred for use in industrial strains because the regulatory authorities in most countries object to the use of antibiotic markers in view of the potential risks of spread of antibiotic-resistance genes in the biosphere upon large-scale use of production strains carrying such genes.

The amdS gene has been used as a dominant marker even in fungi known to contain an endogenous amdS gene, i.e. *A. nidulans* (Tilburn et al. 1983, Gene 26: 205–221) and *A. oryzae* (Gomi et al. 1991, Gene 108: 91–98). In these cases the background of non-transformants can be suppressed by the inclusion of CsCl in the selection medium. In addition, high-copynumber transformants are provided with a growth advantage over the non-transformants (when acetamide is the sole nitrogen-source) because of the higher gene dosage.

Apart from the *A. nidulans* and *A. oryzae* amdS genes, by coincidence a sequence was found in the genome of the yeast *Saccharomyces cerevisiae*, which shows homology to the *A. nidulans* amdS gene (Chang and Abelson 1990, Nucleic Acids Res. 18:7180). The yeast amdS-like sequence was shown not to be essential in yeast. It is, however, not known whether the yeast amdS-like gene actually encodes a protein with amidase activity which might allow to use the gene as selectable marker. amdS genes have not been found in other fungi, despite attempts to detect such genes with heterologous hybridization using the *A. nidulans* amdS gene as probe (see e.g. Kelly and Hynes 1985 EMBO J. 4: 475–479). This is also in line with the observation that, in contrast to *A. nidulans* and *A. oryzae*, most fungi grow very poor, if at all, on acetamide (see e.g. Beri and Turner 1987, Curr. Genet. 11: 639–641; Pentillä et al. 1987, Gene 61: 155–164). The cloning and sequencing of two bacterial acetamidase genes has been reported, i.e. those of *Pseudomonas aeruginosa* (Brammar et al. 1987, FEBS Lett. 215: 291–294) and of *Mycobacterium smegatis* (Mahenthiralingam et al. 1993, J. Gen. Microbiol. 139:

575–583). However, these bacterial acetamidases appear to be unrelated to the above mentioned fungal acetamidases since no sequence similarities can be detected and the bacterial acetamidases are also much smaller than their fungal counterparts. No reports of the use of these bacterial acetamidases as selectable markers have appeared.

In addition to its dominant character, the amdS selectable marker provides the advantage of being a bidirectional marker. This means that, apart from the positive selection for the presence of the amdS gene using acetamide as sole carbon- or nitrogen-source, a counterselection can be applied using fluoracetamide to select against the presence of the amdS gene (Hynes and Pateman 1970, Mol. Gen. Genet. 108, 107–106). The fluoracetamide counterselection has been applied to cure genetically engineered strains from recombinant constructs carrying the amdS gene (e.g. Ward et al. 1993, Appl. Microbiol. Biotechnol. 39, 738–743).

A disadvantage of the amdS marker is the fact that the *A. nidulans* amdS gene is a heterologous gene in industrial fungi such as *A. niger, A. oryzae, T. reesei* and *P. chrysogenum*. Even though this may seem trivial to most molecular biologists, regulatory authorities often object that production strains containing the heterologous *A. nidulans* amdS gene posses a new (the gene being heterologous) and unnecessary (the marker gene not being necessary once the transformant strain is obtained) property, the risks of which cannot be foreseen. Unfortunately, the only industrial filamentous fungus for which an homologous amdS gene is available is *A. oryzae.*

We have previously addressed this problem by developing a method to obtain recombinant fungal production strains that are free of selectable markers (EP-A-0 635 574). In this method the bidirectionality of the amdS marker is used to remove the marker from specially constructed expression cassettes once they have been introduced in the fungal genome. The method is, however, less compatible with the high copy numbers which are often necessary in industrial production strains. For these situations, a homologous and dominant selectable marker would still be required.

SUMMARY OF THE INVENTION

The present invention discloses novel DNA sequences encoding acetamidase genes from fungi other than *Aspergillus nidulans, Aspergillus oryzae* and *Saccharomyces cerevisiae.*

Preferably, these DNA sequences encode acetamidases which comprise an internal consensus fragment, the amino acid positional identity of which is less than 100% when compared with each of the amino acid sequences of SEQ ID NO:1, SEQ ID NO:2, and SEQ ID NO:3, whereas this amino acid positional identity is more than 30% when compared with one of the amino acid sequences of SEQ ID NO:1, SEQ ID NO:2, SEQ ID NO:3, SEQ ID NO:4, and SEQ ID NO:5.

The invention also discloses recombinant DNA constructs comprising the DNA sequences encoding the acetamidases of the invention, as well as recombinant cells containing these constructs.

The invention further discloses recombinant cells in which an endogenous copy of the gene encoding the acetamidase of the invention has been inactivated.

In a further embodiment, the invention discloses a process in which the recombinant cells of the invention are cultured in order to obtain a product of interest.

Finally, the invention discloses methods for obtaining the acetamidase genes of the invention, as well as methods for the inactivation of endogenous copies of these acetamidase genes.

BRIEF DESCRIPTION OF THE FIGURES

FIG. 1A:

Figure 2:
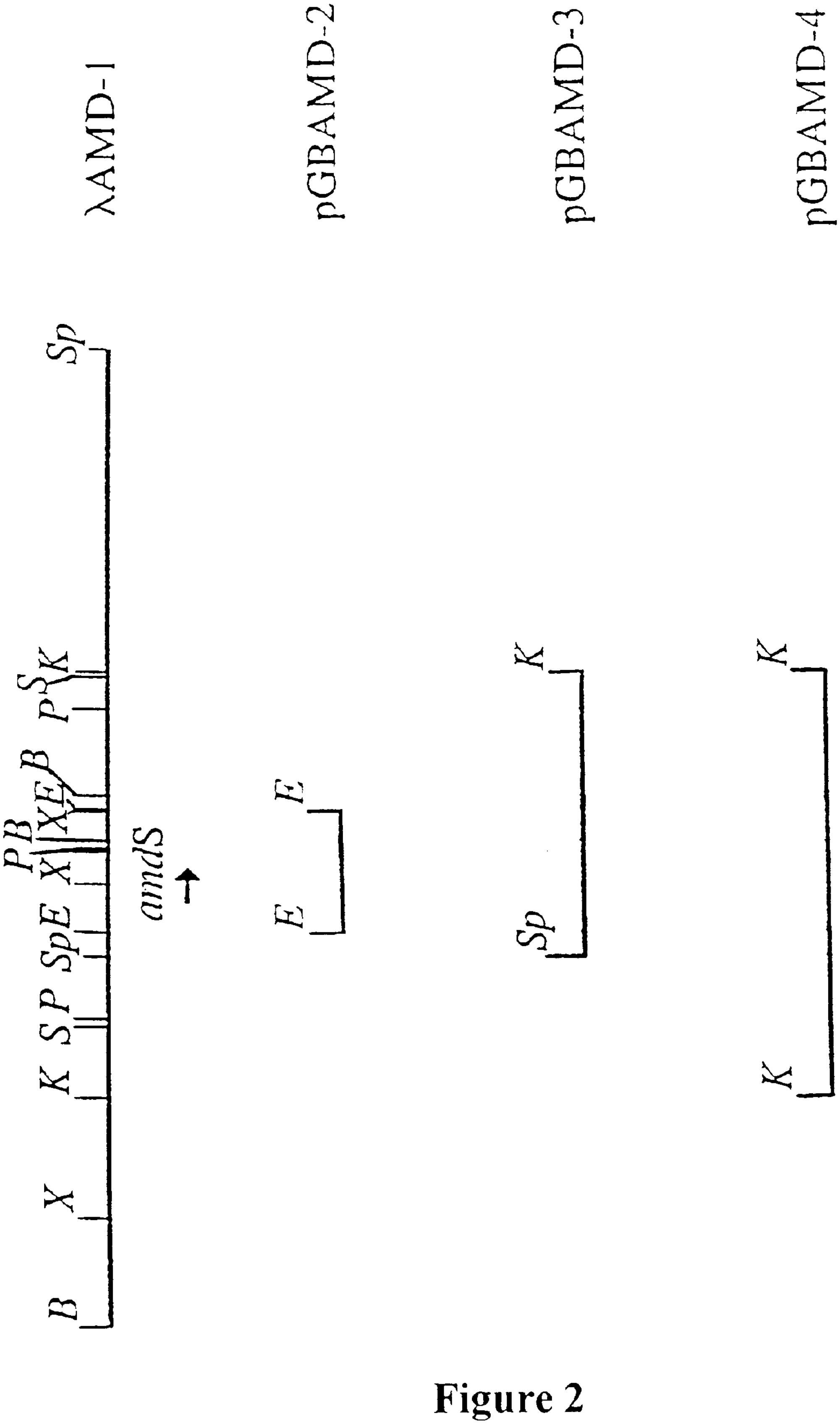

Amino acid comparison of amdS internal consensus fragments of the amdS genes from *A. nidulans, A. oryzae, S. cerevisiae, A. niger* and *P. chrysogenum.*

FIG. 1B:

Amino acid positional identities between each of the amdS internal consensus fragments of FIG. 1A.

FIG. 2:

Partial restriction map of the phage clone λAMD-1 and the subclones pGBAMD-2, pGBAMD-3 and pGBAMD-4. Abbreviations used for the restriction enzymes: B=BamHI, X=XbaI, P=PstI, S=SmaI, Sp=SpeI, K=KpnI, E=EcoRI.

FIG. 3:

BamHI digests of two pGBAMD-4 transformants (lanes 1 and 2), two pGBAMD-3 transformants (lanes 3 and 4) and the parental strain *A. niger* CBS 513.88 (lane 5) probed with a $^{32}P$ labelled EcoRI/BamHI fragment isolated from pGBAMD-1.

FIG. 4:

shows schematically the amdS gene replacement vector pGBAMD-11. Abbreviations used for the restriction enzymes: B=BamHI, Sp=SpeI, K=KpnI, E=EcoRI, S=SmaI, N=NotI, H=HindIII.

DETAILED DESCRIPTION OF THE INVENTION

Several terms used in the present description and claims are defined as follows.

The term gene is herein defined as a DNA sequence encoding a polypeptide, irrespective of whether the DNA sequence is a cDNA or a genomic DNA sequence which may contain one or more introns.

The term selection marker gene (or selectable marker gene) is herein defined as a gene which encodes a polypeptide that provides a phenotype to the cell containing the gene such that the phenotype allows either positive or negative, selection or screening of cells containing the selection marker gene. The selection marker gene may be used to distinguish between transformed and non-transformed cells or may be used to identify cells having undergone recombination or other kinds of genetic modifications.

An acetamidase is herein defined as an enzyme which is capable of catalysing the hydrolysis of acetamide into acetic acid and ammonium, and/or which is capable of catalysing the hydrolysis of related amide-compounds such as acrylamide or ω-amino acids.

An amdS gene is herein defined as a gene, which is preferably obtainable from a eukaryote, more preferably from a fungus, and which encodes a polypeptide that is an acetamidase as defined above. Preferably an amdS gene shows sequence similarity with one or more of the three amdS genes known in the art, i.e. the amdS genes from *A. nidulans, A. oryzae* or the amdS-like gene from *S. cerevisiae.* A more accurate description of the sequence similarity using the amino acid positional identity of an amdS internal consensus fragment is provided below. An amdS gene preferably encodes a protein of about 500 to 600 amino acids, more preferably of about 520 to 570 amino acids and most preferably of about 540 to 550 amino acids. An amdS gene is therefore usually contained within a DNA fragment of about 2.0 kb. Of course the presence of introns in a genomic amdS gene can increase the length to e.g about 2.5 kb or more.

The terms homologous gene is herein defined as a gene which is obtainable from a strain which belongs to the same species, including variants thereof, as does the strain actually containing the gene. Preferably, the donor and acceptor strain are the same. It is to be understood that the same applies to polypeptides encoded by homologous genes. Fragments and mutants of genes are also considered homologous when the gene from which the mutants or fragments are derived is a homologous gene. Also non-native combinations of regulatory sequences and coding sequences are considered homologous as long as the coding sequence is homologous. It follows that the term heterologous herein refers to genes or polypeptides for which donor and acceptor strains do not belong to the same species or variants thereof.

The term endogenous gene is herein defined as a naturally occurring copy of a gene in the genome of the organism in question.

The term fungus herein refers to all members of the division Eumycota of the kingdom Fungi and thus includes all filamentous fungi and yeasts.

In view of recent changes in the nomenclature of black Aspergilli, the term *Aspergillus niger* is herein defined as including all (black) Aspergilli that can be found in the *Aspergillus niger* Group as defined by Raper and Fennell (1965, In: The Genus Aspergillus, The Williams & Wilkins Company, Baltimore, pp 293–344). Similarly, also for the other Aspergillus species we will refer to the Aspergillus groups as defined by Raper and Fennell supra, thereby including all species and variants included in a particular group by these authors.

The present application describes the cloning of amdS genes from fungi not previously known to contain an amdS gene. A comparison of the three available amdS sequences was used to identify conserved regions in the amdS amino acid sequences. The conserved regions are herein defeined as short peptide fragments, e.g. 3–12 or more amino acids, which show a high degree of conservation, i.e. more than 80% identity, in the amino acid sequences of acetamidases from different organisms and which can be used to identify novel acetamidase genes, thereby relying on the fact that in the novel acetamidase these peptide fragments will also be conserved. On the basis of these conserved regions degenerate oligonucleotides were designed which were used as primers in experiments using Polymerase Chain Reactions (PCR) on genomic DNA isolated from *A. niger* and *P. chrysogenum*. Under certain PCR conditions amplified fragments were obtained which were subcloned and sequenced. The sequence analysis clearly identified the amplified PCR fragment as derived from the amdS genes of *A. niger* and *P. chrysogenum* by virtue of the homology of the encoded amino acid sequences to the known (translated) amdS amino acid sequences (see FIG. 1A).

The *A. niger* and *P. chrysogenum* amdS-PCR fragments, which only contained a small part of the amdS genes (approximately 500 and 400 bp, respectively), were used as hybridization probes to screen genomic libraries of *A. niger* and *P. chrysogenum* in order to obtain cloned genomic DNA fragments containing the entire amdS gene for these fungi (see e.g. FIG. 2 for *A. niger*). Restriction fragments in the genomic clones that hybridized to the PCR probes were subcloned into plasmids and subjected to sequence analysis. The resulting nucleotide sequences of the genomic amdS genes of *A. niger* and *P. chrysogenum* are presented in SEQ ID NO:18 and SEQ ID NO:19, respectively. In the absence of the corresponding cDNA sequences we cannot determine the exact positions of the introns in these genomic sequences. We have therefore not deduced the predicted amino acid sequences. Nevertheless, translation of all three reading frames of the genomic sequences allows to identify several areas (in addition to those corresponding to the above mentioned PCR fragments which encode the internal consensus fragments), which have significant amino acid positional identity with the known amdS amino acid sequences.

The present disclosure of the presence of amdS genes in *A. niger* and *P. chrysogenum* provides an incentive for the identification of amdS genes in other organisms, preferably fungi, which at present are not known to contain an amdS gene. The preferred candidates in this respect are the industrially important fungi such as the filamentous fungi belonging to the *Aspergillus niger* group, the *Aspergillus glaucus* group, the *Aspergillus terreus* group, the *Aspergillus restrictus* group, the *Aspergillus fumigatus* group, the *Aspergillus cervinus* group, the *Aspergillus ornatus* group, the *Aspergillus clavatus* group, the *Aspergillus versicolor* group, the *Aspergillus ustus* group, the *Aspergillus wentii* group, the *Aspergillus ochraceus* group, the *Aspergillus candidus* group, the *Aspergillus cremeus* group, the *Aspergillus sparsus* group, Trichoderma species such as *T. reesei* and *T. harzianum*, Mucor species such as *M. miehei*, Rhizopus species, Phanerochaete species, Neurospora species, Humicola species, Claviceps species, Sordaria species, Ustilago species, Fusarium species, Schizophyllum species, Penicillium species such as *P. chrysogenum*, Cephalosporium species, Acremonium species and edible fungi such as *Agaricus bisporus*, and yeasts such as Kluyveromyces species, Yarrowia species, Candida species, Hansenula and Pichia species. As many of the above fungi grow in their natural habitat by decomposing plant material, it is not unlikely that also plants will express genes involved in the metabolism of compounds like acetamide. Hence, plants may also contain an acetamidase gene.

The amdS genes of the invention show sequence similarity with other amdS (-like) genes. This sequence similarity is best defined by the amino acid positional identity of an internal consensus fragment within proteins encoded by amdS genes. The internal consensus fragment is the DNA (or protein) fragment which corresponds to a fragment in the *A. nidulans* amdS gene which encodes amino acids 125 to 226 (or the corresponding protein fragment), the amino acid sequence of which is provided in SEQ ID NO:1. For the determination of the amino acid positional identity, the (encoded) amino acid sequences of the internal consensus fragments are lined up, introducing gaps if necessary for maximal identity, as is shown in FIG. 1A. The amino acid positional identity of two amdS sequences is subsequently expressed as the percentage of identical amino acids in the sequence of the complete internal consensus fragment of the shortest of the two amdS sequences (FIG. 1B). Using the amino acid positional identity, the amdS genes of the invention are defined as DNA sequences encoding proteins which comprise an amino acid sequence of which the amino acid positional identity with each of the amino acid sequences of SEQ ID NO:1, SEQ ID NO:2, and SEQ ID N3 is less than 80%, preferably less than 90%, more preferably less than 95, and most preferably less than 100%, and of which the amino acid positional identity with one of the amino acid sequences of SEQ ID NO:1, SEQ ID NO:2, SEQ ID NO:3, SEQ ID NO:4, and SEQ ID NO:5 is more than 30%, preferably more than 35, more preferably more than 40 and most preferably more than 45%.

The novel amdS sequences of the present invention can be used in conjunction with the already available amdS sequences to more accurately define the conserved regions in the amdS amino acid sequences and type of substitutions occurring therein. This will facilitate the design of improved degenerate oligonucleotides which will increase the chance of obtaining new amdS genes in PCRs or hybridization experiments.

Even though the preferred method for cloning new amdS genes is the method of the present invention, i.e. the use of degenerate oligonucleotides in a PCR on genomic DNA (or cDNA) and subsequent hybridization-screening of DNA (genomic- or cDNA) libraries to obtain the full length amdS gene, other methods can also be used for the cloning of new amdS genes. Such methods may include inverse PCR, heterologous hybridization, hybridization with (degenerate) oligonucleotides, (heterologous) complementation of amdS-negative mutants, or even screening of expression-libraries with suitable antibodies.

The novel amdS genes of the invention, e.g. those from *A. niger, P. chrysogenum*, or one of the other fungi mentioned above, can be used as a homologous selectable marker gene, which is herein understood to mean that the amdS gene is used to select transformants of the same species as the species from which the amdS gene was originally derived. This offers the advantage that the transformants obtained do not contain a foreign selectable marker gene. In principle this allows to construct recombinant strains which contain no foreign DNA other than absolutely necessary, i.e. the (heterologous) gene of interest to be expressed.

In a further embodiment of the invention, the native promoter of the homologous amdS gene is replaced by a different promoter. This replacement promoter, which is referred to as foreign promoter herein, can either be stronger than the native amdS promoter or it can be regulated in a different manner. Either way, the replacement of the native amdS promoter is intended to facilitate the selection of transformants, e.g. by increasing the growth advantage of transformants over non-transformants when grown on acetamide or related amide-compounds as sole N- or C-source. Preferably the foreign promoters are also homologous to the host in which they are used. Suitable foreign promoters can be derived from genes encoding glycolytic enzymes or enzymes involved in alcohol metabolism, such as the promoters from genes encoding phosphoglycerate kinases, glyceraldehyde-phosphate dehydrogenases, triose-phosphate kinases, pyruvate kinase or alcohol dehydrogenases.

In yet a further embodiment of the invention, the sequences of the novel amdS gene are used to inactivate the endogenous copy (or copies) of the amdS gene in the genome of the organism from which the novel amdS gene is derived. To this extent an inactivation vector can be constructed using the sequences of the novel amdS gene to target the vector to an endogenous copy of the gene by homologous recombination. The inactivation can then be caused either by replacement of, or by insertion into the endogenous amdS gene. Inactivation of the endogenous amdS gene provides the advantage of reducing the background of non-transformed cells in transformations using an amdS gene as selectable marker for the introduction of a gene of interest. Alternatively, the endogenous amdS locus can serve as a defined site of integration for genes of interest to be expressed.

The homologous amdS genes of the invention can be used in many different transformation procedures available to the skilled person, including inter alia direct transformation of integrating as well as autonomously replicating vectors, cotransformations in which the DNA to be transformed and the selectable marker are not physically linked, and transformation and subsequent curing of transformants in order to obtain MARKER GENE FREE™ recombinant strains as outlined in EP-A1-O 635 574, which is herein incorporated by reference.

The invention also discloses a method of culturing cells, at least a proportion of which consists of cells according to the invention, in a culture medium, wherein the culture medium comprises acetamide as sole carbon and/or nitrogen source, as well as a method wherein said culturing results in the enrichment of the proportion of cells according to invention.

The invention further discloses living cells according to the invention, preferably fungal cells, with the ability to grow well on a culture medium containing acetamide as sole carbon and/or nitrogen source and wherein said ability is not caused by the expression of a heterologous acetamidase gene but is rather caused by the expression, preferably overexpression, of a homologous acetamidase gene. The ability of a cell to grow well on a culture medium containing acetamide as sole carbon and/or nitrogen source is herein defined as the ability to grow faster than the corresponding wild-type cell, wherein wild-type is understood to mean wild-type with respect to its acetamidase genotype.

The present invention allows the preparation of recombinant cells which contain a recombinant homologous amdS gene, and/or which do not contain an active copy of an endogenous amdS gene. Usually these recombinant cells will further comprise genes of interest to be expressed and/or endogenous genes of interest which have been inactivated. Any one of these recombinant cells can be used in processes for the production of a product of interest. Such a process will usually include the steps of culturing the recombinant cells in a medium conducive to the production of the product of interest and recovery of the product of interest from the culture medium. The products of interest can be proteins, such as an enzyme, and/or primary metabolites, such as $CO_2$, alcohol or organic acids, and/or secondary metabolites, such as antibiotics or carotenoids. The product of interest can also be the recombinant cells themselves, i.e. the biomass obtained in the process.

The following examples are given to illustrate the present invention.

EXAMPLES

Experimental

General Molecular Cloning Techniques

In the examples described herein, standard molecular cloning techniques such as isolation and purification of nucleic acids, electrophoresis of nucleic acids, enzymatic modification, cleavage and/or amplification of nucleic acids, transformation of *E.coli*, etc., were performed as described in the literature (Sambrook et al. (1989) "Molecular Cloning: a laboratory manual", Cold Spring Harbour Laboratories, Cold Spring Harbour, N.Y.; Innis et al. (eds.) (1990) "PCR protocols, a guide to methods and applications" Academic Press, San Diego). Synthesis of oligodeoxynucleotides and DNA sequence analysis were performed on an Applied Biosystems 380B DNA synthesizer and 373A DNA sequencer, respectively, according to the user manuals supplied by the manufacturer.

Transformation of *A. niger*

Transformation of *A. niger* was performed according to the method described by Tilburn, J. et.al. (1983) Gene 26, 205–221 and Kelly, J. & Hynes, M. (1985) EMBO J., 4, 475–479 with the following modifications:

spores were grown for 16 hours at 30° C. in a rotary shaker at 300 rpm in Aspergillus minimal medium. Aspergillus minimal medium consists of the following components: Per liter: 6 g $NaNO_3$; 0.52 g KCl; 1.52 g $KH_2PO_4$; 1.12 ml 4M KOH; 0.52 g $MgSO_4.7H_2O$; 10 g glucose; 1 g casaminoacids; 22 mg $ZnSO_4.7H_2O$; 11 mg $H_3BO_3$; 5 mg $FeSO_4.7H_2O$; 1.7 mg $CoCl_2.6H_2O$; 1.6 mg $CuSO_4.5H_2O$; 5 mg $MnCl_2.4H_2O$; 1.5 mg $Na_2MoO_4.2H_2O$; 50 mg EDTA; 2 mg riboflavin; 2 mg thiamine.HCl; 2 mg nicotinamide; 1 mg pyridoxine. HCl; 0.2 mg panthotenic acid; 4 μg biotin; 10 ml Penicillin (5000 IU/ml)/Streptomycin (5000 UG/ml) solution (Gibco).

only Novozym 234 (Novo Industri), and no helicase, was used for formation of protoplasts;

after protoplast formation (60–90 minutes), KC buffer (0.8 M KCl, 9.5 mM citric acid, pH6.2) was added to a volume of 45 ml. and the protoplast suspension was centrifuged at 2500 g at 4° C. for 10 minutes in a swinging-bucket rotor. The protoplasts were resuspended in 20 ml. KC buffer. Then, 25 ml of STC buffer (1.2 M sorbitol, 10 mM Tris-HCl pH7.5, 50 mM $CaCl_2$) was added and subsequently the protoplast suspension was centrifuged at 2500 g at 4° C. for 10 minutes in a swinging-bucket rotor, washed in STC-buffer and resuspended in STC-buffer at a concentration of $10^8$ protoplasts/ml;

to 200 μl of the protoplast suspension the DNA fragment, in a volume of 10 μl in TE buffer (10 mM Tris-HCl pH7.5, 0.1 mM EDTA), was added and subsequently 100 μl of a PEG solution (20% PEG 4000 (Merck), 0.8 M sorbitol, 10 mM Tris-HCl pH7.5, 50 mM $CaCl_2$);

after incubation of the DNA-protoplast suspension at room temperature for 10 minutes, 1.5 ml PEG solution (60% PEG 4000 (Merck), 10 mM Tris-HCl pH7.5, 50 mM $CaCl_2$) was added slowly, with repeated mixing of the tubes. After incubation at room temperature for 20 minutes, the suspensions were diluted with 5 ml STC buffer, mixed by inversion and centrifuged at 2000 g at room temperature for 10 minutes. The protoplasts were resuspended gently in 1 ml 1.2 M sorbitol and plated onto selective regeneration medium consisting of Aspergillus minimal medium without riboflavin, thiamine.HCL, nicotinamide, pyridoxine.HCl, panthotenic acid, biotin, casaminoacids and glucose but with 10 mM acetamide as the sole nitrogen source, 1 M sucrose, solidified with 2% bacteriological agar #1 (Oxoid, England).

Following growth for 6–10 days at 30° C., the plates were replica plated onto selective acetamide plates consisting of Aspergillus selective regeneration medium with 2% glucose instead of sucrose and 1.5% agarose instead of agar. Single transformants were isolated after 5–10 days of growth at 30° C.

Isolation of Chromosomal DNA from Aspergillus.

The isolation of DNA from Aspergillus was performed according to the procedure as described by Yelton, et al. (1984), Proc. Natl. Acad. Sci. 81, 1470–1474.

Construction of a Genomic Library of *Aspergillus niger* CBS 513.88

Chromosomal DNA isolated from *A. niger* CBS 513.88 was partially digested with Sau3AI, ligated to the BamHI sites of the λEMBL3 arms (e.g. Promega), packaged and transfected to *E.coli* according to Sambrook et al. (1989) "Molecular Cloning: a laboratory manual", Cold Spring Harbour Laboratories, Cold Spring Harbour.

Construction of a Genomic Library of Penicillium Chrysogenum

Chromosomal DNA isolated from *P. chrysogenum* Wisconsin 54–1255 was partially digested with Sau3AI. Fragments with length varying between 7–12 Kb were ligated to the artificially created BamHI sites of the λZAPII arms (e.g. Stratagene), packaged and transfected to *E.coli* according to Sambrook et al. (1989) "Molecular Cloning: a laboratory manual", Cold Spring Harbour Laboratories, Cold Spring Harbour.

Counter-selection on Fluoracetamide

Removal of the *A. nidulans* amdS selection marker is achieved by internal recombination between the 3'-*A. niger* amdS non coding repeats that flank the *A. nidulans* amdS selection marker. Selection of cells that have lost the amdS selection marker is achieved by growth on plates containing fluoracetamide. Cells harbouring the amdS gene metabolize fluoracetamide to ammonium and fluoracetate which is toxic to the cell so only cells that have lost the amdS gene are able to grow on plates containing fluoracetamide.

In case of removal of the amdS marker from Aspergillus transformants, spores from these transformants were plated onto selective regeneration medium (described above) containing 32 mM fluoracetamide and 5 mM ureum instead of 10 mM acetamide, 1.1% glucose instead of 1 M sucrose and 1.1% instead of 2% bacteriological agar #1 (Oxoid, England). After 7–10 days of growth at 35° C. single colonies were harvested and plated onto 0.4% potato dextrose agar (Oxoid, England).

Example 1

Cloning of the amdS of *Aspergillus niger* CBS 513.88

Example 1.1

Synthesis of an amdS Specific PCR Fragment

Oligonucleotide mixes corresponding to the coding and the non-coding DNA strands were designed in well conserved amino acid sequences of the amdS genes from *Aspergillus nidulans* (Corrick M. C., Twomey A. P., Hynes M. J. (1987) Gene 53 63–71), *Aspergillus oryzae* (Gomi K., Kitamoto K., Kumagai C. (1991) Gene 108 91–98) and the amdY gene from *Saccharomyces cerevisiae* (Chang T. H., Abelson J. (1990) Nucleic Acids Res. 18 7180. These oligonucleotide mixes have the following sequences:

```
4078:5' CGG GAT CCG CNT TTT GTA ANA GNG CNG C 3'(SEQ ID NO:6)
                         C   CC   C

4079:5' CGG GAT CCN ATT AGN CTN AAG GAT CA 3'    (SEQ ID NO:7)
                      C TC  T     A   C
                      A

4080:5' GGA ATT CCC TCN CCN CCN CTN CTN CC 3'    (SEQ ID NO:8)
                  T             GA  GA

4081:5' GGA ATT CTA ATN CTN CCN CC 3'            (SEQ ID NO:9)
                 GT      GA
                  G

4082:5' GGA ATT CCN CCA ATA TCN GTN CC 3'        (SEQ ID NO:10)
                      G   G
                      T
```

The oligonucleotide mixes were used in PCR with chromosomal DNA from *A. niger* CBS 513.88 as template. The combinations of two oligonucleotide mixes 4078/4082; 4079/4080 and 4079/4082 (100 pmole each) respectively, were used in reactions with a 50 μl reaction volume also containing 0.5 μg chromosomal DNA from *A. niger* CBS 513.88, 100 nmole dNTP's, Amplitaq reaction buffer (Perkin Elmer) and 1 U Amplitaq (Perkin-Elmer). The conditions for PCR were as follows: After denaturation for 1 min at 94° C., at 72° C. the Amplitaq is added. Next, 30 cycles each 2 min. 94° C.; 2 min. x° C. (x=65°–50° C.; every two cycles×decreases with 1° C.) and 3 min. 72° C. were carried out finally followed by 7 min. 72° C.

The reaction products were analyzed by electrophoresis using an 1% TBE-agarose gel. Only the combination of oligonucleotide mixture 4078 and 4082 resulted in a reaction product, which was approximately 500 bp in length. This PCR fragment was digested with BamHI and EcoRI, purified by agarose electrophoresis and ethanol precipitation and cloned into the BamHI and EcoRI sites of pTZ18R (United States Biochemicals). The resulting plasmid was designated pGBAMD-1.

Example 1.2

Screening of the *Aspergillus niger* CBS 513.88 Genomic Library for the amdS Gene An *A. niger* CBS 513.88 genomic library, constructed in λ-EMBL3 as described in the experimental section, was screened using the $^{32}$P-labelled EcoRI/BamHI fragment isolated from pGBAMD-1. Hybridization with the $^{32}$P-labelled EcoRI/BamHI fragment isolated from pGBAMD-1 took place overnight at 65° C. in hybridization buffer containing 4×SSC, 5× Denhardt's solution, 0.1% SDS and 100 μg/ml heat denatured calf thymus DNA. After hybridization, the filters were washed in 4×SSC/0. 1% SDS, 2×SSC/0.1% SDS and 1×SSC/0.1% SDS at 65° C.

Four plaques, hybridizing with the PCR fragment were identified and isolated and purified. These phage clones were designated λAMD1–λAMD4.

Example 1.3

Restriction Analysis of amdS Containing Phage Clones λAMD1–λAMD4

A partial restriction map was constructed for one of t clones, i.e. λAMD1. The isolated phage DNA was digested with several restriction enzymes, run on a 0.7% agarose gel, blotted onto nitrocellulose (0.2 μm; Schleicher & Schull) and hybridized with the $^{32}$P-labelled EcoRI/BamHI fragment isolated from pGBAMD-1. From the results obtained, a partial restriction map was constructed (see FIG. 2).

Example 1.4

Subcloning Fragments of Phage Clone λAMD-1

Phage clone λAMD-1 contained an insert that was supposed large enough to comprise the entire amdS gene. Several fragments from this phage clone λAMD-1 were subcloned into either pTZ18R or pTZ19R (United States Biochemicals). First, an approximately 2.3 kb EcoRI fragment was isolated from λAMD-1 by digestion of the phage DNA by EcoRI, followed by agarose electrophoresis. The fragment was cloned into the EcoRI site of pTZ18R. The resulting plasmid was designated pGBAMD-2.

Next, the approximately 5 kb SpeI/KpnI fragment was isolated by digesting the phage DNA with SpeI and KpnI followed by agarose electrophoresis. The approximately 5 kb SpeI/KpnI fragment was cloned into the XbaI and KpnI sites of pTZ19R. In this cloning step both the SpeI and the XbaI sites are destroyed. The resulting plasmid was designated pGBAMD-3.

Finally, the approximately 8 kb KpnI fragment was isolated by digesting the phage DNA with KpnI followed by agarose electrophoresis. The isolated fragment was cloned into the KpnI site of pTZ19R. The resulting plasmid was designated pGBAMD-4. A schematic overview of the different subclones is given in FIG. 2.

Example 1.5

Sequence Analysis of the *A. niger* amdS Gene

In order to determine whether the isolated PCR fragment was a part of the *A. niger* amdS gene, the sequence of this fragment was determined (presented in SEQ ID NO:16), translated to an amino acid sequence and compared to the amino acid sequences of the *A. nidulans, A. oryzae* amdS genes and the *S. cerevisiae* amdY gene (see FIG. 1A). A considerable homology was found between the PCR fragment and part of the amdS and amdY genes. Therefore it was concluded that the PCR fragment is a part of the *A. niger* homologue of the amdS gene. To obtain the entire genomic nucleotide sequence of the *A. niger* amdS locus, the sequence of part (about 2.8 kb) of the SpeI/KpnI DNA fragment of pGBAMD-3 was determined as well. This sequence is presented in SEQ ID NO:18.

Example 2

Use of the *A. niger* amdS Gene as Selection Marker Gene in Transformation of *A. niger* CBS 513.88

In order to determine whether the *A. niger* homologue of the *A. nidulans* amdS gene could be used as a selection marker gene in transformations of *A. niger*, DNA from subclones pGBAMD-2, pGBAMD-3 and pGBAMD-4 containing probably the entire coding region of the *A. niger* amdS gene with more or less of the regulatory sequences (promoter and terminator sequences) was used to transform *A. niger* CBS 513.88 according to the method described in the experimental section.

Example 2.1

Transformation of *A. niger* CBS 513.88 with Subclones pGBAMD-2, pGBAMD-3 and pGBAMD-4

From the plasmids pGBAMD-2, pGBAMD-3 and pGBAMD-4 10 μg, 20 μg and 50 μg plasmid DNA was transformed to *A. niger* CBS 513.88 according to the method described in the experimental section. Only with plasmids pGBAMD-3 and pGBAMD-4 transformants could be generated that were able to grow on acetamide as sole nitrogen source.

Example 2.2

Genetic Analysis of *A. niger* pGBAMD-3 Resp. pGBAMD-4 Transformants

To verify that the generated transformants were genuine transformants that had taken up the plasmid DNA two *A. niger*/pGBAMD-3 transformants and two *A. niger*/pGBAMD-4 transformants were analysed using Southern analysis. From these transformants and from the untransformed *A. niger* host strain, high molecular weight DNA was isolated, digested with BamHI, separated by agarose gelelectrophoresis and blotted onto nitrocellulose. The blotted DNA was hybridized with the $^{32}P$ labelled EcoRI/BamHI fragment isolated from pGBAMD-1. The results are presented in FIG. 3.

Figure 3:
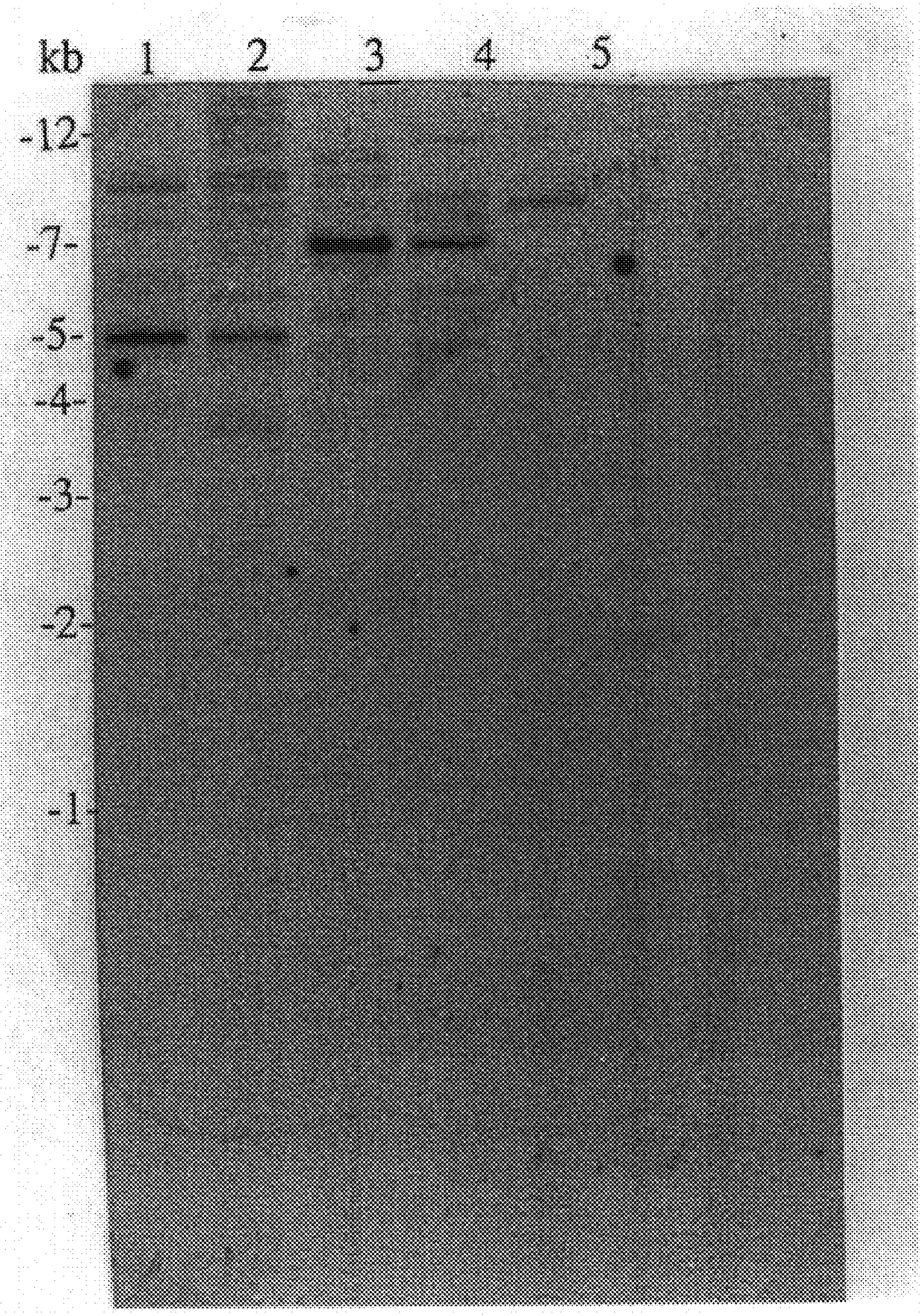
Figure 4:
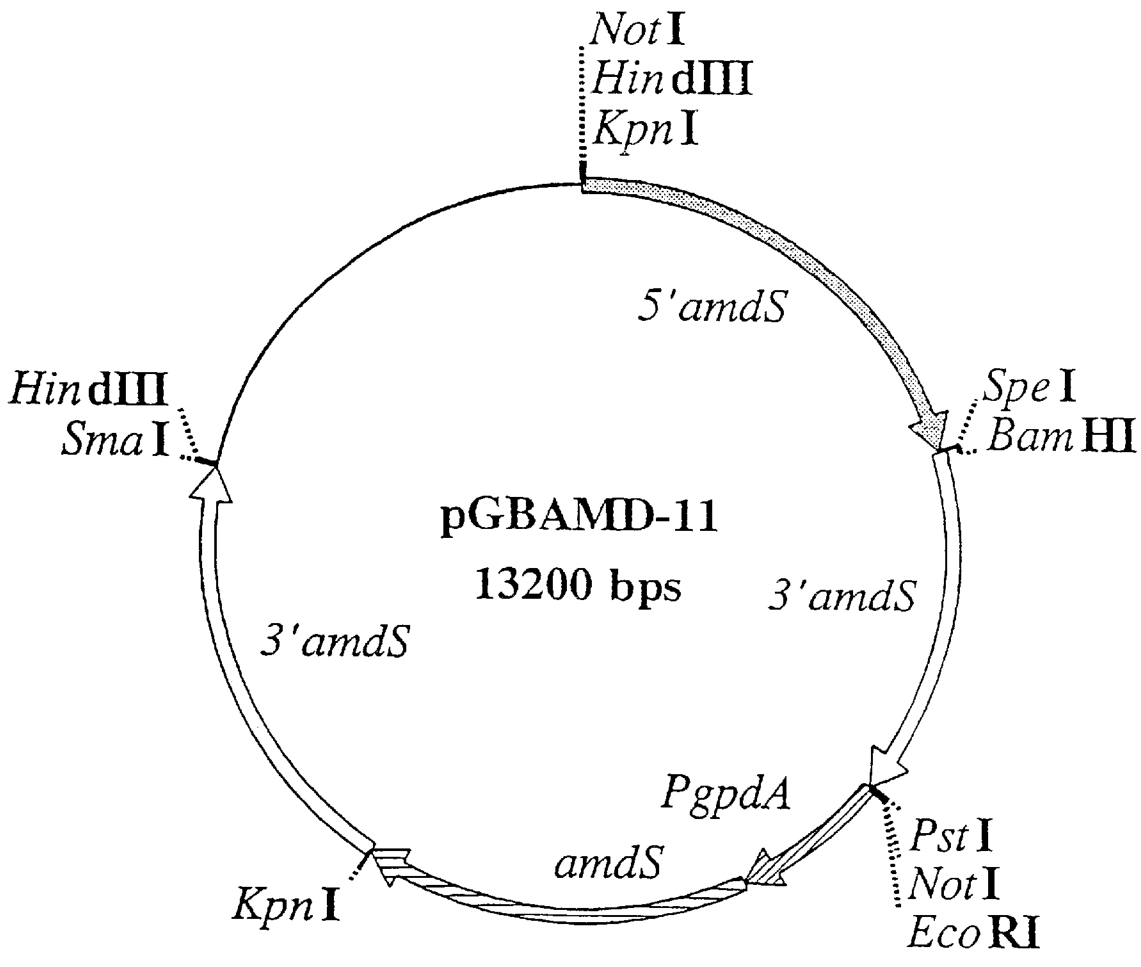

Characteristic for the endogenous amdS gene is an approximately 9 kb hybridizing fragment (see FIG. 3, lane 5). Characteristic for the presence of the pGBAMD-3 plasmid is an approximately 5 kb hybridizing fragment and characteristic for the presence of the pGBAMD-4 plasmid is an approximately 7.5 kb hybridizing fragment. As can be seen in FIG. 3, lanes 3, 4, and lanes 1, 2, hybridizing fragments characteristic for the presence of pGBAMD-3 and pGBAMD-4, respectively, are detected in the transformants. Therefore it can be concluded that the *A. niger* amdS gene can be used as selection marker gene in transformations of *A. niger.*

Example 3

Marker Gene Free™ Deletion of the *A. niger* amdS Gene

This example describes the deletion of the *A. niger* amdS coding region and a (proximal) part of the amdS promoter with a replacement vector which integrates into the *A. niger* genome via a double cross-over homologous recombination. The replacement vector comprises a DNA region homologous to the target locus interrupted by a selectable marker gene flanked by DNA repeats.

The replacement vector comprises a part of the *A. niger* amdS genomic locus, wherein the amdS coding sequences as well as a part of the amdS promoter sequences are replaced by the *A. nidulans* amdS gene under control of the *A. nidulans* gpdA promoter as selection marker flanked by 3'-untranslated *A. niger* amdS sequences as direct repeats. Transformation of *A. niger* with this vector directs the replacement of the *A. niger* amdS gene by the *A. nidulans* amdS gene. By performing the fluoracetamide counter-selection on these transformants as described in the experimental procedures, the *A. nidulans* amdS gene is properly deleted by an internal recombination event between the 3'-*A. niger* amdS repeats, resulting in a MARKER GENE FREE™ ΔamdS recombinant strain, containing no foreign DNA sequences at all.

Example 3.1

Construction Pathway of the amdS Gene Replacement Vector

The first steps in the construction pathway of the *A. niger* amdS gene replacement vector is the construction of a plasmid with a suitable multiple cloning site. To achieve this, the plasmid pTZ18R (United States Biochemicals) was digested with EcoRI and HindIII and the approximately 2.8 kb fragment was purified by agarose electrophoresis and ethanol precipitation and in this fragment two different synthetic fragments of two oligonucleotides were cloned. One synthetic fragment comprises the recognition sites for the restriction enzymes NotI, EcoRI, KpnI, Bg/II, SmaI and HindIII and has the following sequence:

```
5' AATTG GCGGCCGC GAATTC GGTACC AGATCT ATAG GGGCCC A 3'     (SEQ ID NO:11)
      | |||||||| |||||| |||||| |||||| |||| |||||| |
3'      C CGCCGGCG CTTAAG CCATGG TCTAGA TATC CCCGGG TTCGA 5' (SEQ ID NO:12)
```

The resulting plasmid was designated pGBAMD-5.

The other synthetic fragment comprises the recognition sites for the restriction sites NotI, HindIII, KpnI, SpeI, BamHI, PstI, and NotI and has the following sequence:

```
5' AATTG GCGGCCGC AAGCTT GGTACC ACTAGT GGATCC GCAA CTGCAG-
      | |||||||| |||||| |||||| |||||| |||||| |||| ||||||
    3' C CGCCGGCG TTCGAA CCATGG TGATCA CCTAGG CGTT GACGTC-

         GCGGCCGC T 3' (SEQ ID NO:13)
         |||||||| |
         CGCCGGCG ATCGA 5' (SEQ ID NO:14)
```

The resulting plasmid was designated pGBAMD-6.

Next, the approximately 2.5 kb in size BamHI/SmaI fragment from pGBAMD-4, comprising the supposed 3' non-coding region of the *A. niger* amdS gene was cloned into the Bg/II and SmaI sites of pGBAMD-5. In this cloning step both the Bg/II and the BamHI sites were destroyed. The new plasmid was designated pGBAMD-7. This plasmid was digested with EcoRI and KpnI and in these sites the approximately 3.1 kb fragment comprising the *A. nidulans* amdS gene under control of the *A. nidulans* gpdA promoter, isolated from pGBGLA25 (EP 0 635 574 A1), was ligated. The new plasmid was named pGBAMD-8.

Plasmid pGBAMD-6 was digested with BamHI and PstI and in these sites was ligated the approximately 2 kb BamHI/PstI fragment isolated from pGBAMD-4 and comprising part of the supposed 3' non-coding region of the amdS gene. The resulting plasmid was named pGBAMD-9.

Next, pGBAMD-9 was digested with KpnI and SpeI and in these sites was ligated the approximately 2.7 kb KpnI/SpeI fragment isolated from pGBAMD-4 and comprising part of the 5' promoter region of the amdS gene. The resulting plasmid was named pGBAMD-10.

Finally, plasmid pGBAMD-8 was digested with NotI and in this site was ligated the approximately 4.7 kb fragment isolated from pGBAMD-10 and comprising a 5' part of the promoter region and part of the 3' non-coding sequence both of the amdS gene. The resulting plasmid with the cloned fragment in the correct orientation is named pGBAMD-11 and is the replacement vector that is used to delete the *A. niger* amdS gene using the MARKER GENE FREE™ approach.

Example 3.2

Inactivation of the Endogenous *A. niger* amdS Gene

Prior to transformation of *A. niger* with pGBAMD-11, the *E.coli* sequences were removed by HindIII digestion and agarose gel electrophoresis. The *A. niger* strain CBS 513.88 (deposited Oct. 10, 1988) was transformed with either 2.5, 5 or 10 μg DNA fragment by procedures as described in experimental procedures using acetamide as sole N-source in selective plates. Single *A. niger* transformants were purified several times onto selective acetamide containing minimal plates. Spores of individual transformants were collected by growing for about 5 days at 30° C. on 0.4% potato-dextrose (Oxoid, England) agar plates. Southern analyses were performed to verify the presence of the truncated amdS locus.

Example 3.3

Removal of the *A. nidulans* amdS Selection Marker Gene by Counter-selection on Fluoracetamide Containing Plates.

The *A. nidulans* amdS gene in the generated transformants was removed again as described in the Experimental section. Correct removal of the *A. nidulans* amdS selection marker gene was verified by Southern analyses of chromosomal DNA of several fluoracetamide resistant strains.

Example 4

Cloning of the *Penicillium chrysogenum* amdS Gene

Example 4.1

Amplification of an Internal Fragment of the *Penicillium chrysogenum* amdS Gene Using Degenerate Oligonucleotides in a PCR on Genomic DNA At first, the same oligonucleotide combinations were used as described in example 1.1. The oligonucleotide mixtures were used in PCR with chromosomal DNA from, *P. chrysogenum* Wisconsin 54–1255 as template. The conditions for PCR were exactly the same as described in example 1.1.

It was found that oligonucleotide mixtures with oligo AB4082 gave several reaction products. However, oligo AB 4082 itself also could generate a PCR product of the expected molecular size. Therefore it was decided to make a slightly different degenerate oligonucleotide i.e. oligo AB 5224 (SEQ ID NO:15):

```
Oligo AB5224:  5' GGAATTCCAATNCTNCCNCCAATATC 3'
                            TG   GA      G  G
                             T            T
```

The new combination of oligonucleotides AB4079 and AB5424 gave a distinct PCR product; the other combinations of oligonucleotides were not successful.

The PCR product obtained was cloned using the 'InVitroGen' TA cloning kit. Cloned PCR fragments were further characterized by DNA sequence analysis (see SEQ ID NO:17). These DNA sequences were analyzed for ORF's. The amino acid sequence as presented in SEQ ID NO:5 was the result of this analysis. It was concluded that the cloned PCR fragment was part of the *P. chrysogenum* amdS gene. The plasmid with the cloned PCR fragment was called pPENAMDS2.

This PCR fragment was used to clone the entire *P. chrysogenum* amdS gene, which can subsequently be used as homologous selectable marker and/or to inactivate the endogenous *P. chrysogenum* amdS gene as we have outlined above for the *A. niger* amdS gene.

Example 4.2

Screening of the *Penicillium chrysogenum* Genomic Library for the amdS Gene

A *P. chrysogenum* Wisconsin 54–1255 genomic library, constructed in λ-ZAPII (Stratagene, San Diego) as described in the experimental section, was screened using the $^{32}$P-labelled EcoRI fragment isolated from pPENAMDS2. Hybridization with the $^{32}$P-labelled EcoRI fragment took place overnight at 65° C. in hybridization buffer containing 4×SSC, 5×Denhardt's solution, 0.1% SDS and 100 μg/ml heat denatured calf thymus DNA. After hybridization, the filters were washed in 4×SSC/0.1% SDS, 2×SSC/0.1% SDS and 1 ×SSC/0.1% SDS at 65° C.

One plaque, hybridizing with this probe was identified, isolated and purified. This phage clone was designated λPENAMD1.

Example 4.3

Sub-cloning and Restriction Analysis of amdS Containing Phage Clone λPENAMD1

Sub-cloning was done according the protocol of the λ-ZAPII system (Stratagene, San Diego). The result of the sub-cloning experiment is a plasmid that exists of the pBluescript SK vector and an insert of *P. chrysogenum* chromosomal DNA (pPENAMDS101). A partial restriction map was constructed for clone pPENAMDS101. The isolated plasmid DNA was digested with several restriction enzymes, run on a 0.7% agarose gel, blotted onto nitrocellulose (0.2 μm; Schleicher & Schull) and hybridized with the $^{32}$P-labelled EcoRI fragment isolated from pPENAMDS2. From the results obtained, a partial restriction map was constructed.

Example 4.4

Subcloning and Sequencing of the Pc amdS Containing Fragment of Plasmid pPENAMDS101

Plasmid clone pPENAMDS101 contained an NruI-SalI insert of 3.3 Kb that was supposed large enough to comprise the entire amdS gene. The NruI/SalI fragment of pPENAMDS101 was isolated by digesting the plasmid DNA with NruI and SalI followed by agarose electrophoresis. The approximately 3 kb NruI/SalI fragment was ligated in the pBluescript IIKS vector that was already digested with SalI and SmaI. After ligation and transformation in *E.coli* InvαF, transformants were screened using restriction analysis. The resulting plasmid was designated pPENAMDSFL. The result of the DNA sequence analysis of clone pPENAMDSFL is given in SEQ ID NO:19.

What is claimed is:

1. A purified and isolated nucleic acid molecule that comprises an acetamidase-encoding nucleotide sequence that is selected from the group consisting of SEQ ID NO:18 and SEQ ID NO:19.

2. A recombinant nucleic acid molecule that comprises an acetamidase-encoding nucleotide sequence that is selected from the group consisting of SEQ ID NO:18 and SEQ ID NO:19.

3. A recombinant nucleic acid molecule that comprises an acetamidase-encoding nucleotide sequence that is selected from the group consisting of SEQ ID NO:18 and SEQ ID NO:19, said encoding nucleotide sequence operably linked to a promoter.

4. The recombinant nucleic acid molecule of claim 3, wherein said promoter is foreign to said encoding sequence.

5. The recombinant nucleic acid molecule of claim 4, wherein said promoter is from a gene encoding a glycolytic enzyme or a gene encoding an enzyme involved in alcohol metabolism.

6. The recombinant nucleic acid molecule of claim 4, wherein said promoter is from the same species as the acetamidase-encoding sequence.

7. A recombinant host cell which comprises the recombinant nucleic acid molecule of claim 3.

8. A method to produce an acetamidase, which method comprises culturing the cell of claim 7 so as to produce said acetamidase.

9. A fungal cell wherein the acetamidase-encoding nucleotide sequence of claim 1 has been inactivated.

10. The cell of claim 9, wherein said inactivation is the result of homologous recombination.

11. The cell of claim 10, wherein the homologous recombination is a gene replacement.

12. The cell of claim 11, which further comprises a second recombinant DNA.

13. A process for the production of a product encoded by the second recombinant DNA of claim 12, which process comprises the steps of:

a) culturing said cell under conditions conducive to the production of the product encoded by said second recombinant DNA, and b) recovering the product.

* * * * *

```
                              SEQUENCE LISTING

(1) GENERAL INFORMATION:

   (iii) NUMBER OF SEQUENCES: 19


(2) INFORMATION FOR SEQ ID NO:1:

     (i) SEQUENCE CHARACTERISTICS:
          (A) LENGTH: 102 amino acids
          (B) TYPE: amino acid
          (C) STRANDEDNESS: single
          (D) TOPOLOGY: linear

    (xi) SEQUENCE DESCRIPTION: SEQ ID NO:1:

 Pro Ile Ser Leu Lys Asp Gln Leu Arg Val Lys Gly Tyr Glu Thr Ser
  1               5                  10                  15

 Met Gly Tyr Ile Ser Trp Leu Asn Lys Tyr Asp Glu Gly Asp Ser Val
             20                  25                  30

 Leu Thr Thr Met Leu Arg Lys Ala Gly Ala Val Phe Tyr Val Lys Thr
         35                  40                  45

 Ser Val Pro Gln Thr Leu Met Val Cys Glu Thr Val Asn Asn Ile Ile
     50                  55                  60

 Gly Arg Thr Val Asn Pro Arg Asn Lys Asn Trp Ser Cys Gly Gly Ser
 65                  70                  75                  80

 Ser Gly Gly Glu Gly Ala Ile Val Gly Ile Arg Gly Gly Val Ile Gly
                 85                  90                  95

 Val Gly Thr Asp Ile Gly
             100


(2) INFORMATION FOR SEQ ID NO:2:

     (i) SEQUENCE CHARACTERISTICS:
          (A) LENGTH: 102 amino acids
          (B) TYPE: amino acid
```

-continued (C) STRANDEDNESS: single
(D) TOPOLOGY: linear (xi) SEQUENCE DESCRIPTION: SEQ ID NO:2:

```
Pro Ile Ser Leu Lys Asp Gln Leu Arg Val Lys Gly Thr Glu Thr Cys
 1               5                  10                  15

Met Ala Tyr Ile Ser Trp Leu Gly Lys Arg Asp Thr Ser Asp Ser Ile
            20                  25                  30

Leu Thr Ala Leu Leu Arg Lys Ala Gly Ala Val Phe Leu Val Lys Thr
        35                  40                  45

Ser Val Pro Gln Thr Leu Met Val Cys Glu Thr Val Asn Asn Ile Ile
    50                  55                  60

Gly Arg Thr Ser Asn Pro Arg Asn Leu Asn Leu Ser Cys Gly Gly Ser
65                  70                  75                  80

Ser Gly Gly Glu Gly Ala Met Ile Ala Met Arg Gly Gly Ala Ile Gly
                85                  90                  95

Ile Gly Thr Asp Ile Gly
            100
```

(2) INFORMATION FOR SEQ ID NO:3:

(i) SEQUENCE CHARACTERISTICS:
(A) LENGTH: 104 amino acids
(B) TYPE: amino acid
(C) STRANDEDNESS: single
(D) TOPOLOGY: linear (xi) SEQUENCE DESCRIPTION: SEQ ID NO:3:

```
Pro Ile Ser Leu Lys Asp Gln Cys Asn Val Glu Gly Val Asp Thr Ser
 1               5                  10                  15

Leu Gly Tyr Leu Cys Arg Thr Phe Lys Pro Lys Thr Lys Asn Glu Glu
            20                  25                  30

Ser Leu Ile Val Ser Phe Leu Arg Asp Leu Gly Ala Ile Ile Phe Val
        35                  40                  45

Lys Thr Thr Val Pro Ser Ser Met Met Ala Thr Asp Thr Gln Ser Asn
    50                  55                  60

Thr Phe Gly Tyr Thr Tyr Asn Ser Ile Asn Leu Ser Phe Ser Ser Gly
65                  70                  75                  80

Gly Ser Ser Gly Gly Glu Gly Ser Leu Ile Gly Ala His Gly Ser Leu
                85                  90                  95

Leu Gly Leu Gly Thr Asp Ile Gly
            100
```

(2) INFORMATION FOR SEQ ID NO:4:

(i) SEQUENCE CHARACTERISTICS:
(A) LENGTH: 111 amino acids
(B) TYPE: amino acid
(C) STRANDEDNESS: single
(D) TOPOLOGY: linear (xi) SEQUENCE DESCRIPTION: SEQ ID NO:4:

```
Pro Val Ser Leu Lys Asp Gln Phe His Val Lys Gly Val Glu Thr Thr
 1               5                  10                  15

Met Gly Tyr Val Gly Trp Ile Asn Thr Phe Gln Gly Lys Thr Asn Asp
            20                  25                  30

Pro Arg Tyr Leu Thr His Glu Ser Glu Leu Val Lys Glu Leu Arg Ala
        35                  40                  45

Ala Gly Ala Val Leu Tyr Cys Lys Thr Ser Val Pro Met Thr Leu Met
```

-continued

```
    50                  55                  60

Ser Gly Glu Thr Met Asn Asn Ile Ile Thr Tyr Thr His Asn Pro Lys
65                  70                  75                  80

Asn Arg Leu Leu Ser Ser Gly Gly Ser Ser Gly Gly Glu Gly Ala Leu
                85                  90                  95

Ile Ala Leu Arg Gly Ser Pro Ala Gly Phe Gly Thr Asp Ile Gly
            100                 105                 110
```

(2) INFORMATION FOR SEQ ID NO:5:

(i) SEQUENCE CHARACTERISTICS:
(A) LENGTH: 102 amino acids
(B) TYPE: amino acid
(C) STRANDEDNESS: single
(D) TOPOLOGY: linear (xi) SEQUENCE DESCRIPTION: SEQ ID NO:5:

```
Pro Ile Trp Leu Lys Asp Gln Phe Asn Val Lys Gly Val Asp Thr Thr
 1               5                  10                  15

Leu Gly Tyr Val Gly Arg Ser Phe Ala Pro Ala Gln Glu Asp Ala Val
            20                  25                  30

Leu Val Gln Ile Leu Lys Asn Met Gly Ala Ile Val Ile Ala Lys Thr
        35                  40                  45

Asn Ile Pro Gln Ser Ile Met Val Ala Glu Thr Glu Asn Pro Leu Trp
    50                  55                  60

Gly Leu Thr Thr Asn Pro Arg Asn Pro Ile Phe Ser Pro Gly Gly Ser
65                  70                  75                  80

Thr Gly Gly Glu Gly Ala Leu Leu Ala Leu His Gly Ser Leu Phe Gly
                85                  90                  95

Phe Gly Thr Asp Ile Gly
            100
```

(2) INFORMATION FOR SEQ ID NO:6:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:6:

CGGGATCCGC NTTYTGYMAN MGNGCNGC 28

(2) INFORMATION FOR SEQ ID NO:7:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:7:

CGGGATCCNA THWSNYTNAA RGAYCA 26

(2) INFORMATION FOR SEQ ID NO:8:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:8:

-continued

GGAATTCCYT CNCCNCCNSW NSYNCC 26

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:9:

GGAATTCKDA TNSWNCCNCC 20

(2) INFORMATION FOR SEQ ID NO:10:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:10:

GGAATTCCNC CDATRTCNGT NCC 23

(2) INFORMATION FOR SEQ ID NO:11:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:11:

AATTGGCGGC CGCGAATTCG GTACCAGATC TATAGGGGCC CA 42

(2) INFORMATION FOR SEQ ID NO:12:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:12:

AGCTTGGGCC CCTATAGATC TGGTACCGAA TTCGCGGCCG CC 42

(2) INFORMATION FOR SEQ ID NO:13:

(i) SEQUENCE CHARACTERISTICS:
(A) LENGTH: 56 base pairs
(B) TYPE: nucleic acid
(C) STRANDEDNESS: single
(D) TOPOLOGY: linear (xi) SEQUENCE DESCRIPTION: SEQ ID NO:13:

AATTGGCGGC CGCAAGCTTG GTACCACTAG TGGATCCGCA ACTGCAGGCG GCCGCT 56

(2) INFORMATION FOR SEQ ID NO:14:

(i) SEQUENCE CHARACTERISTICS:
(A) LENGTH: 56 base pairs
(B) TYPE: nucleic acid
(C) STRANDEDNESS: single
(D) TOPOLOGY: linear (xi) SEQUENCE DESCRIPTION: SEQ ID NO:14:

-continued

```
AGCTAGCGGC CGCCTGCAGT TGCGGATCCA CTAGTGGTAC CAAGCTTGCG GCCGCC        56
```

(2) INFORMATION FOR SEQ ID NO:15:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:15:

```
GGAATTCYDA TNSWNCCNCC DATRTC                                         26
```

(2) INFORMATION FOR SEQ ID NO:16:

(i) SEQUENCE CHARACTERISTICS:
(A) LENGTH: 542 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (vi) ORIGINAL SOURCE:
(A) ORGANISM: Aspergillus niger
(B) STRAIN: CBS 513.88
(C) INDIVIDUAL ISOLATE: amdS-ICF (xi) SEQUENCE DESCRIPTION: SEQ ID NO:16:

```
CGGGATCCGC GTTTTGCCAT AGTGCAGCAT TGGCGCATCA ACTCGTACAT TCCCCATCCA    60

CAAGGAGTGC TAGTCTGCGC TTTACTAATC GAGAAAAAGG TAAACTGCTT GCATGAAATC   120

TTCTTCGATG CCGCGCTTGA AACCGCCCGC ATTCTAGACG ACCACTACAC CAAGACCGGC   180

AAGCCACTCG GTCCCCTTCA CGGCCTCCCT GTCAGTCTGA AGGATCAATT CCACGTCAAG   240

GGCGTAGAAA CAACCATGGG TTACGTCGGC TGGATAAACA CCTTCCAAGG CAAGACCAAT   300

GACCCGCGCT ATCTTACACA CGAAAGCGAA CTCGTTAAAG AACTCCGCGC CGCGGGAGCC   360

GTCCTCTACT GCAAGACTAG CGTCCCCATG ACGTTGATGT CAGGTGAAAC CATGAACAAT   420

ATCATAACTT ACACACATAA CCCGAAGAAC AGGCTTCTCA GTTCTGGAGG TAGTTCCGGG   480

GGCGAAGGAG CACTGATCGC GTTGCGGGGA TCACCAGCCG GGTTTGGGAC CGATATCGGG   540

GG                                                                  542
```

(2) INFORMATION FOR SEQ ID NO:17:

(i) SEQUENCE CHARACTERISTICS:
(A) LENGTH: 384 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (vi) ORIGINAL SOURCE:
(A) ORGANISM: Penicillium cnrysogenum
(B) STRAIN: Wisconsin 54-1255
(C) INDIVIDUAL ISOLATE: amds-ICF (xi) SEQUENCE DESCRIPTION: SEQ ID NO:17:

-continued

```
CGGGATCCTA TCTGGCTTAA GATCAATTTA ACGTCAAAGG CGTGGACACG ACCCTGGGAT    60
ATGTGGGTAG ATCCTTCGCC CCGGCCCAGG AAGACGCAGT GCTTGTGCAG ATCCTGAAGA   120
ACATGGGTGC CATCGTCATT GCGAAGACAA ATATCCCACA GAGTATCATG GTTCGTCCGA   180
GGTTGTCACT GGCAGTATCT GATTCGGATA TTGACTCTAC CTCCAGCGGG CCGAAACCGA   240
GAATCCTCTC TGGGGACTGA CGACTAACCC TCGCAATCCT ATTTTTTCAC CGGGTGGGTC   300
AACTGGCGGC GAAGGCGCTT TGCTGGCATT GCATGGATCA CTATTCGGAT TTGGGACTGA   360
CATAGGCGGT TCAATAAGAA TTCC                                          384
```

(2) INFORMATION FOR SEQ ID NO:18:

(i) SEQUENCE CHARACTERISTICS:
(A) LENGTH: 2869 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (vi) ORIGINAL SOURCE:
(A) ORGANISM: Aspergillus niger
(B) STRAIN: CBS 513.88
(C) INDIVIDUAL ISOLATE: amdS (xi) SEQUENCE DESCRIPTION: SEQ ID NO:18:

```
TGTATAACAT AGCGGGGTAG CAAGTGCCTG TCAGCTTGGC GCCCATCTAT CCATCCATCT    60
ACCATTCATT CATCTCCATC TTCATCTCCA TTTCACCCAA ATAATGCAGA ATTCCCAATT   120
GTCGCCGCCC CGTATCTCCT CCCTATCTCA TCGATAACTC AAGTCCGAGC ACTATCTGTC   180
TCCGCGCATC AAACAAGCTA ATTCTCCCCA GGATGGATGA TAAGCAAGAT ATATTCCGCG   240
CCATTGGCTC CACTTCCTGC AATCCCCCGC CTTCATATGA CTGACGAATA GCAAGAATAG   300
GTAAGACAAC GGGATGATCA TCCCACCGAA CGCATTGATA AGAAAGGCCC TATGGTCCAC   360
CCCCTCTTTA TTTACCATCT TATCCCCTCA AGACATCCAC CTCCGCAACA GATACTCCTA   420
CAACCACTGC TTTCAAAATG GCCCTCACAT CCTGGGAACA AACCGCAGCG GCCAAACGCC   480
AATCCGTCCT CAACGCCATC CCCGAGAAAT GGCGCATCAA GGGTCCTATC CCCGCACCGT   540
CGGAGCAGCG CGACGTAACA GGCCCCTACA TCCAGCAGTT CCTATCCCCA CGCGAGGTTG   600
AAATCACCGA AACAGACGCC GTAGGGATCA CAGAGCGAAC TACAACGGGC CAGTGGACAG   660
CTGTGGAGGT GACCGAGGCG TTCTGCCATC GCGCAGCATT GGCGCATCAA CTCGTACATT   720
CCCCATCCAC AAGGAGTGCT AGTCTGCGCT TTACTAATCG AGAAAAAGGT AAACTGCTTG   780
CATGAAATCT TCTTCGATGC CGCGCTTGAA ACCGCCCGCA TTCTAGACGA CCACTACACC   840
AAGACCGGCA AGCCACTCGG TCCCCTTCAC GGCCTCCCTG TCAGTCTGAA GGATCAATTC   900
CACGTCAAGG GCGTAGAAAC AACCATGGGT TACGTCGGCT GGATAAACAC CTTCCAAGGC   960
AAGACCAATG ACCCGCGCTA TCTTACACAC GAAAGCGAAC TCGTTAAAGA ACTCCGCGCC  1020
GCGGGAGCCG TCCTCTACTG CAAGACTAGC GTCCCCATGA CGTTGATGTC AGGTGAAACC  1080
ATGAACAATA TCATAACTTA CACACATAAC CCGAAGAACA GGCTTCTCAG TTCTGGAGGT  1140
AGTTCCGGGG GCGAAGGAGC ACTGATCGCG TTGCGGGGAT CACCAGCCGG GTTTGGTACG  1200
GATATCGGGG GTAGTATCCG TGTTCCTGCG TCGTTCAATG GACTGTATGG GATACGGCCG  1260
TCTGTGGGGA GAATGCCGTA CGAGGGGGCG GCCAATTCGG GCGATGGACA GAATACTGTG  1320
```

-continued

```
TTGTCGGTTG TGGGGCCGTT GTCTCCTTCG GCGAGAGGGT TGATATTGCT GTTCAAGACG  1380
GTGTTGGGGG CAATGCCGTG GTTGGGAGAT CCTGGTGTGT TGGAGATTCC CTGGAGGGAG  1440
GAAATCGTAG AGGAGACGAG AAAATTAGTG CAGGGAAAGC CAGAGGGGCT AGCTTTTGGA  1500
ATATTCTACG ATGATGGTCA GGTAAAGCCG CAGCCACCGG TCGAGAGAGC GATGCGGATT  1560
GCTGCAGAGA CGATCAAGCG TCTAGGACAT AAGGTGAGTG CCCTCCTTCT TCTTGCGACA  1620
CTGCTAACAT TCATCCCAGC TCATCAATTG GGAACCCCCC TCTCACCTAA CAGCCGCCTC  1680
CCTCGCAGTA AGTCCCCCAT CCAACCCACT ACACCACAAC CCCCTAACAA TAAACCAACC  1740
CCCAGAACCG CGCCTACAAC ATGGACGGCG GCGCCGACGT ACTCCAAAAC TTCGCCCTGT  1800
CCAACGAAGC CATCCACACC TCCGTAGTAA TCGACGCATC AGGATCCCCC CAAAAGACCG  1860
CACTAGAGAT CGCCGCGCTA AACGTCGAGA AGCGCGAATA CCAGAAACAA TACCTTGACT  1920
ACTGGAACAG CACGGCGCAA TTGACAGGGA CTGGACGACC CGTCGACGCG GTCATTTGTC  1980
CAGTGGCGCC GCATGCGGCG TGCATTCCGG GGAAGTATGC GACGATCGGG TATACGGCGT  2040
TTATTAATGT GTTGGATTAT ACGAGTGCGG TTGTGCCGGT TACGAGTGCT GATAGGAGGG  2100
TGGATGTTGT AGGGAAGGAA GGAAGGGAGT ATTTTGGGGA GTTGGATAGG AAGACCGAGG  2160
GGGAGTGTAA GTTCTTCCCT TTCTTTTCTT CTTTCTTTTC ATTGAGCTAT CCAATTTGGT  2220
TGGAGGTCTT GTGTGTTTGT TTGTTCGGAG AGTGGTGATG GGGTTATGTG CTGACTGGAT  2280
GTTTCTATCT AGACGATGCG GATGTGTTTG ATGGGGCGCC GGCTGGGATT CAGCTCTTTG  2340
GAAGACGGCT TCAGGAGGAG AAGATTCTGG TACTGGCTGA GTATCTTGGT GAGGAATTCA  2400
AGAAGGCTAG TGCTTGATCA TAGCGAGTAG TATGGGAATC GATCAAATTG TCTAGTGATA  2460
TTGAGAGAAA TGCAGTGATG ACACACATTC TGTTGTGAGA AACAGACGAA TATACAACGA  2520
AGCCGAAAAA TGTACAGTTG TAAGTATCAT AGCATCATTA TATCTCTACC ATCCCTCCAG  2580
CGGCGTTACT TTCACACGGA CCCCGTCCTT CGGGGTCACT GTCGCGGCTT CACGGAGTAT  2640
GAGCTCTTTC TTAGGATCCT CGAGTTCAAA CTGGAATCGT CCAACAAATG CGGCCAGCAG  2700
ACAAGCCAGC TCGGCTTTCG CAAAACCCTG CCCAATGCAA CTACGCGGGC CATGTATGAA  2760
GGTCAAAAAG GCGTAGTTGC TGGTGGCACC GCCAGTGTTG GCTTGCCGGG GCCAACCACC  2820
GTCGGGATTG ACTGATCGCA TCAGGGCCCA AGGACTATCG TGGTTGTCA             2869
```

(2) INFORMATION FOR SEQ ID NO:19:

(i) SEQUENCE CHARACTERISTICS:
(A) LENGTH: 3315 base pairs
(B) TYPE: nucleic acid
(C) STRANDEDNESS: single
(D) TOPOLOGY: linear (ii) MOLECULE TYPE: Genomic DNA (iii) HYPOTHETICAL: NO (iv) ANTI-SENSE: NO (vi) ORIGINAL SOURCE:
(A) ORGANISM: Penicillium chrysogenum
(B) STRAIN: Wisconsin 54-1255
(C) INDIVIDUAL ISOLATE: amdS (xi) SEQUENCE DESCRIPTION: SEQ ID NO:19:

```
ATTGTAATAA TTTTTGGATA ATTTCTAATG AGAGTTTATT ATCAGATTAG CAAAATATCT    60
CTTTCCGAAT GGTCTAATAT ATGTAGCTAT TGAGTGGTAA CTGATTAAGA TCCAAAGGTC   120
```

-continued

```
AAGATAAATC CCCGTTATAT ATAGTGGCTC CCATACTAAA CTCGCGATTA AAATCTTGTC   180
TCACTTTGAA AATTGACAAC CCTCCATCCA AAATACTTAC TGATATAATC TGTGATATAT   240
ATTACATTAG GTTTGTAATG ATAAATAATG ATAAAAAAAA AAAAAAAATG TTACAATATA   300
AATCTATTGA GAGAATAGGG TTCAAGTTGG TCAGTTTTGG TGGGAAAATA GGGAGTGGGA   360
AGATACTTAG TAACAGGGTC TGTATATGTC CCACACTGTA AACGAAGCCA GGCAGGAATG   420
TCAGCCTTCT AATAGACGAG ATTTCACCCC ACAAAGACCC TCGAAATCAA AGATGTCATG   480
GTTAGAGAGA GGACATCAAC AAGATATCCC AATAACCCCT GGACCGAGGC TGTATGTGAA   540
GTATCGAGGC GCTAAACCTA AAAAGGAAAA ACTAACCGGA TACAGTTACA GTAGTTCACT   600
CCGCCGTTTA CAGATTCAAA ATGCTCAAGA ACTCCAAAGA CTCCAAATTA TTTGGGGGGA   660
ACGGCAAATC TCGGTTGGAT AAAGAAAAAA CGAAATTACT CCAAAAATGA CATTTGACGA   720
GAGTGTGCCA CGTCCCCACT TGATAAGAGT GGCCCTCGGA CTACAGTCCG AGCTGACTAT   780
ATTAGGCTAG TCTTGACCTC CAACAGGGCT CTTACAAGTG CAATTCAAAG TAAAATGGGC   840
AGTCAGACCT GGGAGGAGAT TGTCTCCCAG AAACGGGCCA TCAGAGACCA ACTCATCGCA   900
CCGTACTTAG CCGATGTAGC TCAACGTCTG CCGCGAGTAC AGAATGCCGA GGAGCGTACT   960
CGACTAGAAG ATCTGTTGTT TCAAACGATT ACAGACATTG ACAATGTCAC CTCTCTGCTG  1020
GAATGCATGG CGAAAGGAGA GTTCCAGGTA GAACAGGTGA TCAAGGCATA TATCCAACGG  1080
TATGTCTTCT ATCGGGGTTG GAACAGGCCC TATACTAATG CCATCGGTAG GGCTGTGCTA  1140
GCACATCAAT TAGTACGTGT CCCACATCTT CCTTCCTTTC CATTTGCACC CTTGGCCAAG  1200
TCGCTTATAG AATCTGGCAT GGGTAGACAA ATAGCCTGAC CGAGGTTCTT TTTGAAGATG  1260
CCCTAGGACA GGCAAAGCAG CTAGACGCCG AATTTGCAGA AACTGGAAAG CTCAGAGGTC  1320
CCCTGCATGG AATTCCAATC ACGGTGAAAG ACCAATTTAA CGTCAAAGGC GTGGACACGA  1380
CCCTGGGATA TGTGGGTAGA TCCTTCGCCC CGGCCCAGGA AGACGCAGTG CTTGTGCAGA  1440
TCCTGAAGAA CATGGGTGCC ATCGTCATTG CGAAGACAAA TATCCCACAG AGTATCATGG  1500
TTCGTCCGAG GTTGTCACTG GCAGTATCTG ATTCGGATAT TGACTCTACC TCCAGTGGGC  1560
CGAAACCGAG AATCCTCTCT GGGGACTGAC GACTAACCCT CGCAATCCTA TTTTTTCACC  1620
GGGTGGGTCA ACTGGCGGCG AAGGCGCTTT GCTGGCATTG CATGGATCAC TATTCGGATT  1680
TGGGACTGAT ATTGGCGGAA GTGTAAGGAT CCCACAGGCT ACAGTGGGCT TGTACGGATT  1740
CAAACCAAGC GTAAGTACCA ACCGCCATGA ACAAACTGTC CTTTCTTTTC CATTTTTTTA  1800
ATATGTGTCG ATGATTCCTG AAAGCAGAGC GCCCGACTTC CTTACCAGGG CGTACCCGTC  1860
TCCACTGAGG GTCAAGAACA TGTCCCGTCT TCAATCGGCC CGATGGCCCG GGATCTCTCG  1920
TCTATCTGCC ACATGAGCCG TCTGATAGCG AACAGCCAGC CGTGGGATGT TGATCCGCGG  1980
TGCGCTCCTC TTCCTTGGAA TGACACTGCA TTCCAAGAAC TTCAAGTCCG ACCTATGGTA  2040
ATCGGCTTGA TCCTGGATGA CGGTGTAGTA AAGGTCCACC CGCCTATTGC GCGTGCCCTG  2100
CTAGAACTCT CAGCAGTACT TAGAGCACAT GGCCACGAAG TTGTGGTCTG GGATACATTT  2160
GATCATGCGG AGTGCATTGA GATTATGGAT ATCTTCTACA CGGTCGATGG GGGTGAGGAT  2220
ATTCGTCGGG ATGTAGCCGC TGCCGGCGAG CCGTTTATTC CTCATGTTGA AGGGCTGGTT  2280
AACCGCGGCA AGGCTATATC GGTTTATGAG TATTGGCAGC TGAACAAGCG GAAAACTGCA  2340
GTGCAGAAGA AATATCTGGA CAAATGGAAC GCGGTGCGAT CTCCGTCGGG TCGGGCTGTC  2400
GATGTTCTGC TGAGTCCTAC CTTGCCGCAT ACGACTGTGC CTCATCGGAA ATTCCGTTGG  2460
GTTGGCTATA CTAAGATTTG GAATTTGTTG GACTACCCGG CTTTGACGTT CCCAGTGGAT  2520
```

-continued

| | | | | | | |
|---|---|---|---|---|---|---|
| AGAGTGAGGG | CTGAGGTGGA | TGTGTTGCCA | TCGGAGCCTT | ATATCCCGAG | AAACAGCCTC | 2580 |
| GACGAGTGGA | ATTGGAATAT | TTTCGATGCC | AAACAAGCGG | ATGGATGTCC | AGTGAATCTG | 2640 |
| CAGATCATCG | GAAAAAAACT | CCACGAAGAG | AAGGTACTGG | GGGCTGCTAC | AGTTATTGAG | 2700 |
| AGGCTCTGGA | AAAGTCATAT | CGACGAATCC | AATTGAACCA | TCTGGGATGT | ATGGGTAGAA | 2760 |
| AATGAAGTTG | GGTTCACTCG | CAGACTGAAC | GACGTGTATC | GCAGTTGACT | GAACTGAATT | 2820 |
| TGGAATAAAT | ATGGTAGACA | TAACTCATTA | TGCAGCTTGG | TGGGATATCT | GCCTCCAGAG | 2880 |
| TCATATAAAT | CACAAACGCC | GTGGGAATAT | GCAACAAGAC | AAGCACTCTT | GAGTCTCAAG | 2940 |
| CCTTGGGAGG | CTCGAACAGA | TCGGGTTTCA | TGTTAATTTT | GCAAAGCTTC | GCCACACAGC | 3000 |
| CGCTCAGTTG | AAGCAGTGAC | TGCACGCCGT | CTAGTATACG | CATATGCGTG | AATCCAATCT | 3060 |
| CCCGGATAAA | CTCCAACTTG | GAATGTTCAG | ACAATGTGGG | AATGGTCTTG | GTGACTCGGA | 3120 |
| ACATGGTACT | GATGATATCA | TGCGCAGAAT | AACCCAGCGT | CCTGTGGATA | CAAAATGATT | 3180 |
| AGGACCTCCT | GCAGTTGAAC | CAAACAGATG | TGTAACATAC | CATAGCTCGT | TCAACCCCTC | 3240 |
| CAGTGCCACA | TCCACCTTGC | CTTCCCAGCA | AGCCTTGATC | ATGGCCTGGA | CTTTGACCGG | 3300 |
| GTGCGGGCTG | TCGAC | | | | | 3315 |